(12) United States Patent
Shippert (10) Patent No.: US 10,959,755 B2
(45) Date of Patent: Mar. 30, 2021

(54) APPARATUS AND METHOD FOR REMOVING INTRA-OSSEOUS DEVICE

(71) Applicant: Shippert Tech, LLC, Boalsburg, PA (US)

(72) Inventor: Brian Shippert, Boalsburg, PA (US)

(73) Assignee: Shippert Tech, LLC, Boalsburg, PA (US)

( * ) Notice: Subject to any disclaimer, the term of this patent is extended or adjusted under 35 U.S.C. 154(b) by 92 days.

(21) Appl. No.: 16/179,718

(22) Filed: Nov. 2, 2018

(65) Prior Publication Data

US 2019/0125404 A1    May 2, 2019

Related U.S. Application Data

(60) Provisional application No. 62/580,524, filed on Nov. 2, 2017.

(51) Int. Cl.
| | |
|---|---|
| *A61M 31/00* | (2006.01) |
| *A61B 17/34* | (2006.01) |
| *A61B 10/02* | (2006.01) |
| *A61B 17/16* | (2006.01) |
| *A61B 90/00* | (2016.01) |

(52) U.S. Cl.
CPC ........ *A61B 17/3472* (2013.01); *A61B 10/025* (2013.01); *A61B 17/3403* (2013.01); *A61B 17/1637* (2013.01); *A61B 2010/0258* (2013.01); *A61B 2017/3407* (2013.01); *A61B 2017/3492* (2013.01); *A61B 2090/08021* (2016.02); *A61M 2210/02* (2013.01)

(58) Field of Classification Search
CPC ............ A61B 17/3403; A61B 17/3472; A61B 2017/3407; A61B 2017/3492; A61M 2005/3247; A61M 2210/02
See application file for complete search history.

(56) References Cited

U.S. PATENT DOCUMENTS

| | | | | |
|---|---|---|---|---|
| 4,998,924 A | * | 3/1991 | Ranford | A61M 5/3271 604/110 |
| 5,197,953 A | * | 3/1993 | Colonna | A61M 5/3243 604/110 |
| 5,215,535 A | * | 6/1993 | Gettig | A61M 5/28 604/198 |
| 7,699,850 B2 | | 4/2010 | Miller | |
| 2004/0267204 A1 | | 12/2004 | Brustowicz | |
| 2005/0131345 A1 | * | 6/2005 | Miller | A61B 17/3476 604/117 |

* cited by examiner

*Primary Examiner* — Rebecca E Eisenberg
(74) *Attorney, Agent, or Firm* — Sheridan Ross P.C.

(57) ABSTRACT

Apparatuses, systems, and methods are provided for securing an intra-osseous device within a safety device to prevent stick injuries and to guide the removal of the intra-osseous device from the bone of a patient. A body of the safety device has a cavity that receives the intra-osseous device, and the cavity guides the removal of the intra-osseous device along a straight line to prevent injury during removal. The intra-osseous device is drawn past a lock feature that secures the intra-osseous device within the body such that a needle of the intra-osseous device is contained within a cavity of the body and cannot injure the patient, staff members, etc.

19 Claims, 7 Drawing Sheets

APPARATUS AND METHOD FOR REMOVING INTRA-OSSEOUS DEVICE

CROSS REFERENCE TO RELATED APPLICATIONS

The present application claims the benefit of U.S. provisional patent application Ser. No. 62/580,524, filed Nov. 2, 2017, the entire disclosure of which is hereby incorporated herein by reference.

FIELD

The present disclosure provides an apparatus, system, and method for safely removing an intra-osseous device from a body into an enclosed containment unit.

BACKGROUND

Every year, hundreds of thousands of sharps related injuries occur among healthcare workers. For example, according to the Center for Disease Control and Prevention (CDC) over 385,000 sharps related injuries occur annually. Aside from the stress and risk of blood borne pathogens associated with sharps injuries (Hepatitis B, Hepatitis C, Human Immunodeficiency Virus, syphilis, malaria, herpes, etc.), there are healthcare costs: loss of time, testing and treatment also increase costs and place the burden on healthcare workers, employers, and society.

Sharps safety is such a serious issue that the United States Congress passed the Needlestick Safety and Prevention Act and guides regulatory agencies like the Occupational Safety & Health Administration (OSHA) with regard to blood borne pathogen standards and mandates implementation of safer medical devices.

According to the National Institute of Occupational Safety and Health (NIOSH), the design of the device can increase the risk of injury. Specific features make certain devices more dangerous. These include: (NIOSH, 1999) devices with hollow-bore needles, needle devices that need to be taken apart or manipulated by the health care worker such as blood-drawing devices that need to be detached after use, syringes that retain an exposed needle after use, and needles that can be difficult to place in sharps containers.

Safety devices such as needleless or protected-needle systems, needle shielding, and encased needles have been effective at reducing accidental sharp exposures. However, there is a paucity of safety devices for medical apparatuses that gain access to bone marrow. Currently, medical devices that gain access to bone marrow, especially those that insert a penetrator or needle, contain all the specific features of a medical device at high risk for iatrogenic injuries.

Commonly known as intra-osseous devices, these devices present unique characteristics from other medical devices associated with sharps injuries. Since intra-osseous devices must enter cortical bone, they tend to be extremely sharp and typically have more than a single cutting surface or point to increase cortical bone penetration. Intra-osseous devices are typically of a larger caliber than commonly used needles and peripheral vascular access devices. Intra-osseous devices carry greater risk of bodily contamination due to microscopic fractured bone fragments in addition to blood component exposure.

The technique of removal of an intra-osseous medical device is a crucial step for patient and healthcare worker safety. Due to the bone matrix and micro-fractures associated with placement of the medical devices, withdrawal of these devices must occur in the opposite vector of the placement to minimize worsening of the fracture area. Angulation of the device during withdrawal is associated with increased chance of worsening micro-fractures of the bone and increased risk of device failure and lodgment in the subject bone.

The technique of removal can be complicated by initial incorrect placement of an intra-osseous device. Placement in dense cortical bone may necessitate significant force to overcome the initial resistance of the cortical bone. However, once initial resistance is overcome, the force exponentially decreases over a very short interval. The rapid decline in resistance creates another dangerous opportunity for sharps injury; healthcare workers have been known to physically jerk upon the device's release from the bone and potentially impale the worker or assistants during device removal.

SUMMARY

In accordance with the present disclosure, an apparatus, system, and method for consistent and safe removal of an intra-osseous device into an enclosed locking unit are provided. In some embodiments, a safety device is configured to guide the removal of the intra-osseous device from a patient's body along a straight line and/or along the line that the intra-osseous device was inserted into the patient's body. As a result, the intra-osseous device does not damage bone or tissue as the intra-osseous device is removed.

In addition, as the intra-osseous device is removed, the safety device safely houses the intra-osseous device to prevent sharps related injuries to the patient, staff, etc. The intra-osseous device can generally have an aperture through which the intra-osseous device is drawn. The intra-osseous device passes a lock feature on the inner surface of the safety device, and the intra-osseous device is secured between the lock feature and a second end or aperture of the safety device. Once secured, the needle or other similar feature of the intra-osseous device is contained within the safety device to prevent sharps related injuries.

In accordance with one embodiment of the present disclosure, the body of the safety device has a frustum shape. The apex of the frustum has a central aperture with a diameter large enough to accommodate an average 12 mL or smaller syringe. The overall height of the frustum is greater than the length of the intra-osseous device. This allows the intra-osseous device to be completely enclosed in the safety device without the intra-osseous device's trochar or needle protruding outside of the containment of the safety device. Typically the overall height is 1.1-1.2 times the overall length of the intra-osseous device to be removed. An internal spatial volume within said frustum is sufficient for containing and securing the entirety of the intra-osseous device. The base of the frustum has a central aperture with a diameter that is between 1.1-1.2 times the maximum outer diameter of the intra-osseous device. The outer body of the frustum is solid to contain potential biologic material. The cavity within the safety device is cylindrical to maintain the correct vector for intra-osseous device removal. The device retaining and locking mechanism operates as a single unit. There are no intricate parts, no difficult manipulations, and no cumbersome features or structures to control. The safety device is structurally simple and easy to operate.

In accordance with another embodiment of the present disclosure, the body of the safety device has a frustum shape. The apex of the frustum has a central aperture in a diameter large enough to accommodate an average 12 mL or smaller syringe. The overall height of the frustum is greater than the length of the intra-osseous device. This allows the intra-osseous device to be completely enclosed in the device without the intra-osseous device's trochar or needle protruding outside of the containment of the apparatus. Typically, the overall height is 1.1-1.2 times the overall length of the intra-osseous device to be removed. An internal spatial volume within said frustum is sufficient for containing and securing the entirety of the intra-osseous device. The base of the frustum has a central aperture in a diameter 1.1-1.2 times the maximum outer diameter of the intra-osseous device to be removed.

Immediately proximal to the spatial volume required to contain the fully retracted intra-osseous device, is the integral locking mechanism, a ridge of material which constricts the internal circumference of the inner cylinder to a diameter that is smaller than the outer diameter of the intra-osseous device. Two narrow median grooves extend from the base of the frustum to a distance distal to the integral locking device. This distance is propriety to and dependent upon materials in order to allow natural flexing of the safety device to allow passage of the intra-osseous device beyond the locking ring into the fully retracted state. The cavity of the safety device is shaped as a cylinder. This design feature maintains the correct vector for intra-osseous device removal. The device retaining and locking mechanism operates as a single unit. There are no intricate parts, no difficult manipulations, and no cumbersome features or structures to control. The safety device is structurally simple and easy to operate.

In accordance with a further embodiment of the present disclosure, the body of the safety device has a cylindrical shape. One end of the cylinder has a central aperture in a diameter large enough to accommodate an average 12 mL or smaller syringe. The overall height of the cylinder is greater than the length of the intra-osseous device. This allows the intra-osseous device to be completely enclosed in the device without the intra-osseous device's trochar or needle protruding outside of the containment of the apparatus. Typically, the overall height is 1.1-1.2 times the overall length of the intra-osseous device to be removed. An internal spatial volume with said cylinder is sufficient for containing and securing the entirety of the intra-osseous device.

The other end of the cylinder has a central aperture in a diameter 1.1-1.2 times the maximum outer diameter of the intra-osseous device to be removed. The outer body of the cylinder is solid to contain potential biologic material. The cavity of the safety device is shaped as a cylinder. This design feature maintains the correct vector for intra-osseous device removal. The device retaining and locking mechanism operates as a single unit. There are no intricate parts, no difficult manipulations, and no cumbersome features or structures to control. The safety device is structurally simple and easy to operate.

In accordance with an embodiment of the present disclosure, the lock feature is positioned in the containment cylinder of the frustum immediately proximal to the fully retracted intra-osseous device. The locking mechanism is circumferential to allow several independent points of contact preventing disengagement of the intra-osseous device. The locking mechanism is a wedge with the widest portion most proximal to the fully retracted intra-osseous device. The narrowest portion of the wedge functions as the pivot point of the locking mechanism, facilitating movement of the locking mechanism out of the internal cylinder as the intra-osseous device is retracted fully into the containment cylinder. The wedge moves back into the lumen of the cylinder due to the structural integrity of the material the locking mechanism is composed of. With accordant with another embodiment of the present disclosure, the lock feature pushes the locking wedge back into the lumen of the containment cylinder.

One particular embodiment of the present disclosure is an apparatus for securing an intra-osseous device, comprising a body extending from a first end to a second end; a cavity defined by an inner surface of the body, and the cavity extending between a first aperture at the first end of the body and a second aperture at the second end of the body; a lock feature positioned on the inner surface of the body, wherein the lock feature is positioned a first predetermined distance from the first end of the body; and a channel extending from the first end to a distal point that is a second predetermined distance from the first end, wherein the second predetermined distance is larger than the first predetermined distance.

In some embodiments, the lock feature comprises a ramp portion oriented towards the first end of the body and comprises a shoulder portion oriented towards the second end of the body, wherein the shoulder portion extends from the inner surface of the body at a substantially perpendicular angle. In various embodiments, the ramp portion extends from the inner surface of the body at an angle between approximately 30 and 60 degrees. In some embodiments, the lock feature extends continuously along the inner surface of the body between the channel and an additional channel.

In various embodiments, the lock feature is part of a plurality of discrete lock features positioned on the inner surface of the body. In some embodiments, the apparatus further comprises a relief aperture positioned at the distal point of the channel, wherein the relief aperture has an outermost width that is larger than a width of the channel. In various embodiments, the channel extends in a direction that is substantially parallel to a longitudinal axis of the body. In some embodiments, a cross-sectional profile of the lock feature has a semi-circular shape.

Another particular embodiments of the present disclosure is a system for securing an intra-osseous device, comprising a body extending from a first end to a second end; a cavity defined by an inner surface of the body, and the cavity extending between a first aperture at the first end of the body and a second aperture at the second end of the body; a lock feature positioned on the inner surface of the body, wherein the lock feature is positioned a predetermined distance from the first end of the body, and the lock feature defines an inner diameter; and an intra-osseous device having a base portion and a needle, wherein the base portion has an outermost diameter that is larger than the inner diameter defined by the lock feature, and wherein the intra-osseous device is configured to pass the lock feature such that the intra-osseous device is secured within the body and the needle is contained with the cavity.

In various embodiments, wherein the second aperture has an inner diameter that is smaller than the outermost diameter of the base portion such that the intra-osseous device is retained within the body between the second aperture and the lock feature after the intra-osseous device passes the lock feature. In some embodiments, the system further comprises a syringe selectively connected to the intra-osseous device, the syringe having a barrel with an outer diameter that is smaller than an inner diameter of the second aperture. In various embodiments, the inner diameter of the second aperture is between 1.1-1.2 times larger than the outer diameter of the barrel. In some embodiments, an overall length of the intra-osseous device is smaller than an overall length of the body. In various embodiments, a channel extends from the first end to a distal point that is a second predetermined distance from the first end, wherein the second predetermined distance is larger than the predetermined distance of the lock feature.

Yet another particular embodiment of the present disclosure is a method for securing an intra-osseous device in a safety device, comprising providing an intra-osseous device with an outermost diameter; providing a safety device having a body positioned about the intra-osseous device, wherein the body has an inner surface that defines a cavity extending between a first aperture at a first end of the body and a second aperture at a second end of the body, and wherein an inner diameter of the second aperture is smaller than the outermost diameter of the intra-osseous device; providing a lock feature on the inner surface of the body, wherein the lock feature defines an inner diameter that is smaller than the outermost diameter of the intra-osseous device; drawing the intra-osseous device through the body of the safety device towards the second end; and deflecting the lock feature with the intra-osseous device such that the intra-osseous device passes the lock feature and is contained with the cavity.

In some embodiments, the intra-osseous device has an overall length, wherein the overall length of the intra-osseous device is smaller than an overall length of the body of the safety device. In various embodiments, the method further comprises selectively connecting a syringe to the intra-osseous device, wherein the syringe has a barrel with an outer diameter that is less than the inner diameter of the second aperture; and removing the syringe from the intra-osseous device after the intra-osseous device is secured between the lock feature and the second aperture. In some embodiments, the method further comprises fastening the intra-osseous device to an osseous area. In various embodiments, the method further comprises providing a channel in the body of the safety device that extends from the first end to a distal point, wherein the channel allows the lock feature to deflect and permit the intra-osseous device to pass the lock feature. In some embodiments, the lock is positioned a first predetermined distance from the first end of the body, and the distal point of the channel is a second predetermined distance from the first end of the body, wherein the second predetermined distance is larger than the first predetermined distance.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements or components. Additional aspects of the present disclosure will become more readily apparent from the Detailed Description, particularly when taken together with the drawings.

The above-described embodiments, objectives, and configurations are neither complete nor exhaustive. As will be appreciated, other embodiments of the disclosure are possible using, alone or in combination, one or more of the features set forth above or described in detail below.

The phrases "at least one," "one or more," and "and/or," as used herein, are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

Unless otherwise indicated, all numbers expressing quantities, dimensions, conditions, and so forth used in the specification and claims are to be understood as being modified in all instances by the term "about."

The term "a" or "an" entity, as used herein, refers to one or more of that entity. As such, the terms "a" (or "an"), "one or more," and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

BRIEF DESCRIPTION OF THE DRAWINGS

The accompanying drawings, which are incorporated in and constitute a part of the specification, illustrate embodiments of the disclosure and together with the Summary of the Invention given above and the Detailed Description of the drawings given below, serve to explain the principles of these embodiments. In certain instances, details that are not necessary for an understanding of the disclosure or that render other details difficult to perceive may have been omitted. It should be understood, of course, that the disclosure is not necessarily limited to the particular embodiments illustrated herein. Additionally, it should be understood that the drawings are not necessarily to scale.

Similar components and/or features may have the same reference label. Further, various components of the same type may be distinguished by following the reference label by a letter that distinguishes among the similar components. If only the first reference label is used, the description is applicable to any one of the similar components having the same first reference label irrespective of the second reference label.

DETAILED DESCRIPTION

The present disclosure has significant benefits across a broad spectrum of endeavors. It is the Applicant's intent that this specification and the claims appended hereto be accorded a breadth in keeping with the scope and spirit of the disclosure being disclosed despite what might appear to be limiting language imposed by the requirements of referring to the specific examples disclosed. To acquaint persons skilled in the pertinent arts most closely related to the present disclosure, a preferred embodiment that illustrates the best mode now contemplated for putting the disclosure into practice is described herein by, and with reference to, the annexed drawings that form a part of the specification. The exemplary embodiment is described in detail without attempting to describe all of the various forms and modifications in which the disclosure might be embodied. As such, the embodiments described herein are illustrative, and as will become apparent to those skilled in the arts, may be modified in numerous ways within the scope and spirit of the disclosure.

Although the following text sets forth a detailed description of numerous different embodiments, it should be understood that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims. To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning.

Various embodiments of the present disclosure are described herein and as depicted in the drawings. It is expressly understood that although the figures depict safety devices, intra-osseous device, etc., the present disclosure is not limited to these embodiments With reference to FIG. 1A-B, a safety device 100 that includes an enclosure body 104 in accordance with embodiments of the present disclosure is depicted in a perspective view (FIG. 1A) and a cross-sectional view (FIG. 1B) taken along line B-B in FIG. 1A. The enclosure body 104 in this exemplary embodiment is in the form of a cylinder but could be other forms such as a frustum shape. A cavity 108 extends from a first aperture 112 in a bottom or first end 116 of the enclosure body 104 to a second aperture 124 in a top or second end 128 of the enclosure body 104. The first aperture 112 can have a diameter that is larger than the second aperture 124 to accommodate an intra-osseous device as described in further detail below. The cavity 108 defines a chamber with a substantially cylindrical volume, except for a retaining structure or lock feature 136 formed between the first 112 and second 124 apertures.

Figure 1A:
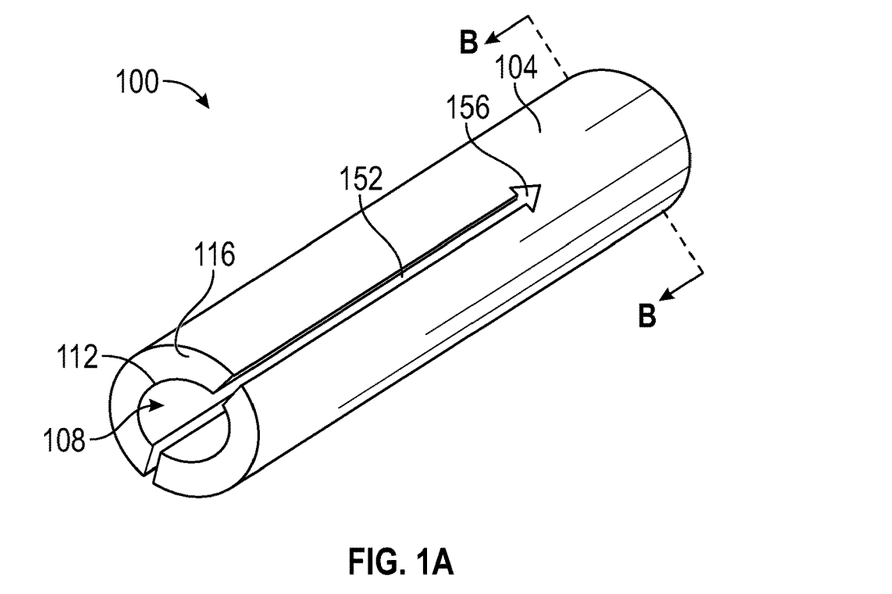
FIG. 1A depicts a perspective view of a safety device for removing and securing an intra-osseous device in accordance with an embodiment of the present disclosure.
Figure 1B:
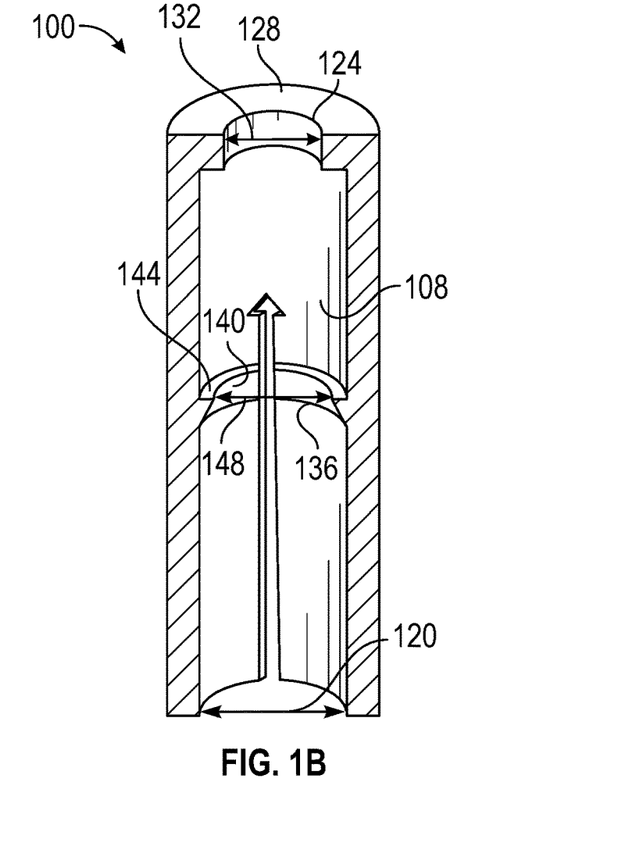
FIG. 1B is a cross-sectional view of the safety device of FIG. 1A taken along line B-B in accordance with an embodiment of the present disclosure.

The lock feature 136 can be in the form of a wedge with a ramp portion 140 facing the first aperture 112 and a shoulder portion 144 facing the second aperture 124. The lock feature 136 can be formed continuously around the inner surface of the body 104, or can be formed as discrete ramp members, with gaps therebetween. In accordance with at least some embodiments of the present disclosure, the enclosure body 104 can include one or more channels 152 that extend from the first end 116 of the body 104 to a point between the lock feature 136 and the second end 128 of the body 104. The channels 152 can increase the flexibility of the body 104, and in particular can facilitate passing a base portion of an intra-osseous device past the lock feature 136 when withdrawing an intra-osseous device from a body, as discussed elsewhere herein. In accordance with at least some embodiments of the present disclosure, an end of each of the channels 152 opposite the first end 116 of the body 104 can have a stress relieving aperture or feature 156.

Also shown in FIG. 1B are an inner diameter 120 of the first aperture, an inner diameter 132 of the second aperture 124, and an inner diameter 148 defined by the lock feature 136. As described below these diameters 120, 132, 148 function with an outermost diameter of an intra-osseous device such that the outermost diameter can freely pass through the inner diameter 120 of the first aperture, pass through the inner diameter 148 of the lock feature 136 with force, and then be retained between the inner diameter 148 of the lock feature 136 and the inner diameter 132 of the second aperture 124.

Figure 2:
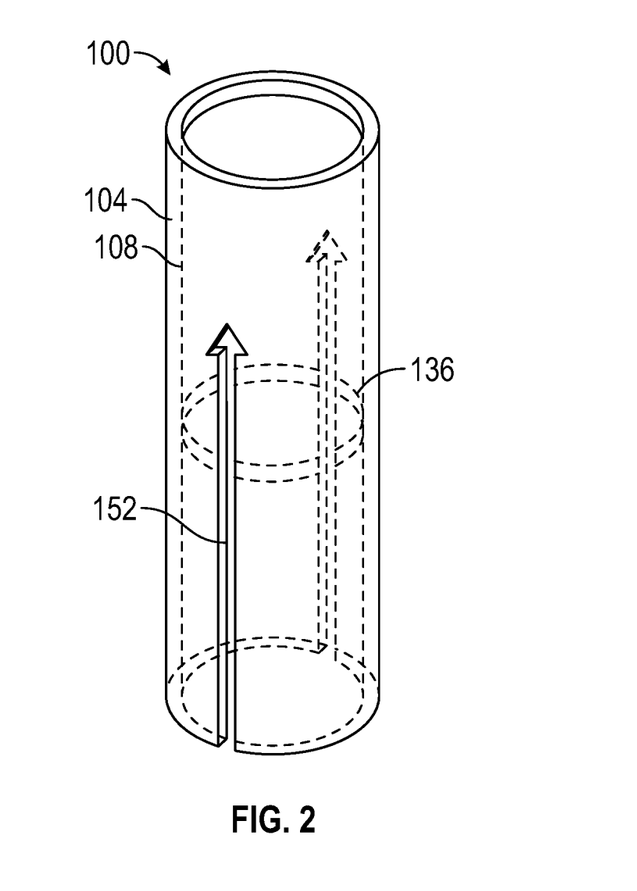
FIG. 2 is a further perspective view of another safety device for removing and securing an intra-osseous device in accordance with an embodiment of the present disclosure.

With reference to FIG. 2, a safety device 100 that includes an enclosure body 104 in accordance with other embodiments of the present disclosure is depicted in a transparent perspective view. The enclosure body 104 in this exemplary embodiment is in the form of a cylinder. Similar to other embodiments of a safety device 100 in accordance with embodiments of the present disclosure, a cavity 108 extends from a first aperture in a bottom or first end of the enclosure body 104 to a second aperture in a top or second end of the enclosure body 104. Also similar to other embodiments of the present disclosure, the cavity 108 can include a containment or primary chamber that defines a substantially cylindrical volume that extends from the first aperture to the second aperture, except for a retaining structure or lock feature 136 formed between the first and second apertures.

Figure 3A:
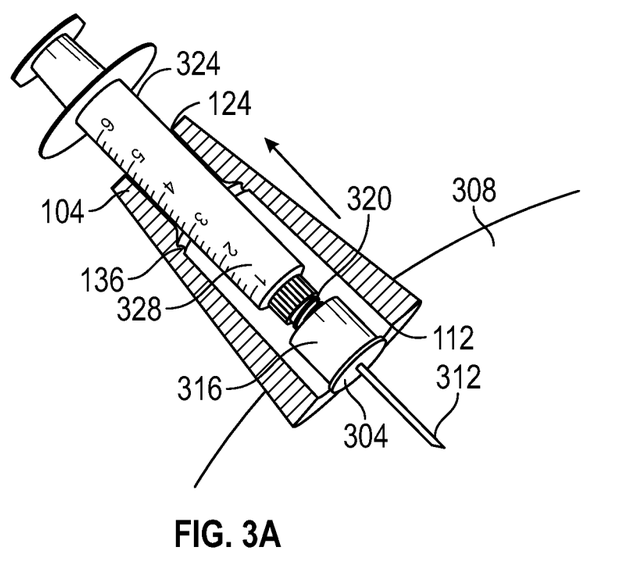
FIG. 3A is a perspective view of a safety device positioned about an intra-osseous device in accordance with an embodiment of the present disclosure.
Figure 3B:
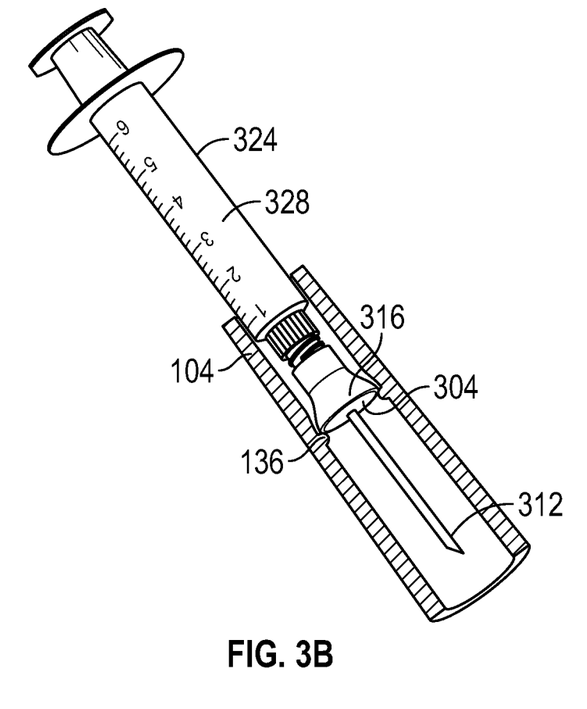
FIG. 3B is a perspective view of a safety device guiding an intra-osseous device during removal in accordance with an embodiment of the present disclosure.
Figure 3C:
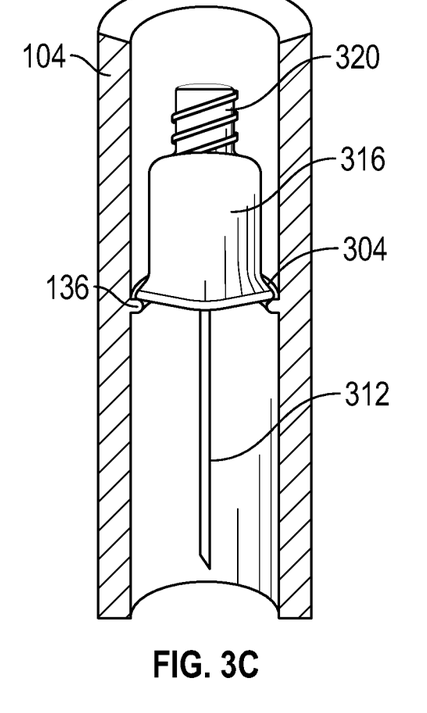
FIG. 3C is a perspective view of a safety device securing an intra-osseous device during removal in accordance with an embodiment of the present disclosure.

With reference now to FIG. 3A-C, a safety device 100 in accordance with embodiments of the present disclosure is shown being used to safely guide and secure an intra-osseous device 304 in a body 104 of a safety device. As can be appreciated by one of skill in the art, the intra-osseous device 304 is typically placed in the patient body 308, and more particularly within an interior portion of a bone, using a drill (not shown) to rotate the intra-osseous device 304. The drill is then disengaged from the intra-osseous device 304. An IV or syringe 324 can then be connected to an attachment mechanism 320, such as a Luer lock, provided by a base portion 316 of the intra-osseous device 304, to enable fluids, such as medications, to be introduced to the patient body 308.

As can be appreciated by one of skill in the art, removing the intra-osseous device 304 from the body is preferably done by pulling the intra-osseous device 304 from the patient body 308 along a line that is coincident with the line along which the intra-osseous device 304 was installed. In addition, the tip of the intra-osseous device 304 is usually extremely sharp, and presents a stick hazard to personnel removing the intra-osseous device 304. A safety device 100 in accordance with embodiments of the present disclosure provides a stabilizing structure for removing the intra-osseous device 304, and further provides containment for the intra-osseous device 304, to avoid contact between the intra-osseous device 304 and users of the safety device 100.

In accordance with embodiments of the present disclosure, a process for removing the intra-osseous device 304 includes placing the first aperture 112 of the enclosure body 104 of the safety device 100 over the base portion 316 of the intra-osseous device 304. A syringe 324 or other removal tool can then be joined to the attachment mechanism 320. In order to facilitate applying a removing force that is coincident or nearly coincident with the line along which the device 304 is installed, the diameter of the first aperture 112 and the primary chamber can be dimensioned so that they are slightly (e.g. 0.5-2 mm) larger than the diameter of the base portion 316 of the intra-osseous device 304. In addition, the second aperture 124 can be dimensioned so that it has a diameter that is slightly (e.g. 0.5-2 mm) larger than a diameter of the syringe 324 barrel 328. The second aperture 124 can also extend along a line that is coincident with a central axis of the enclosure body 104 for some distance (e.g. 5-15 mm) to assist in stabilizing the syringe 324. A physician or other practitioner can then hold the enclosure body 104 against the patient body 308 with one hand, while pulling the syringe 324 barrel 328 away from the patient body 308. As or after the tip of the intra-osseous device 304 is completely withdrawn from the body, the base portion 316 of the intra-osseous device 304 is pulled past the lock feature 136. In accordance with embodiments of the present disclosure, pulling the base portion 316 of the intra-osseous device 304 past the lock feature 136 requires some force, and at least temporarily deforms at least one of the lock feature 136 or the base portion 316. The intra-osseous device 304 is then retained by the lock feature 136, and contained entirely within the interior chamber, for example as depicted in FIG. 3C.

Figure 4A:
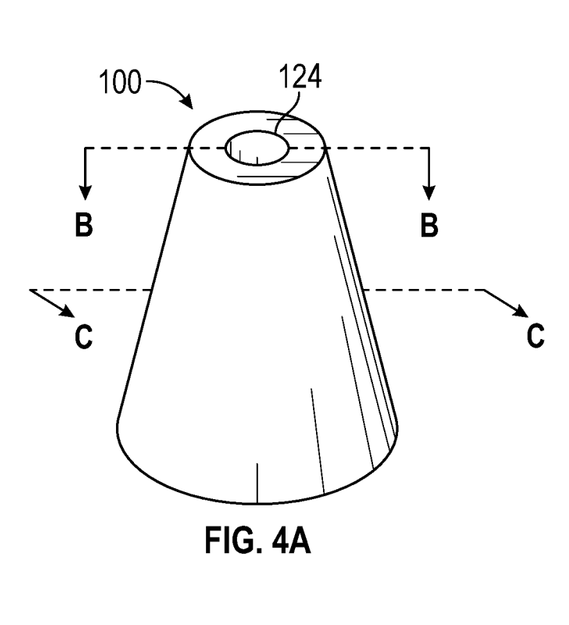
FIG. 4A is a perspective view of another safety device for removing and securing an intra-osseous device in accordance with an embodiment of the present disclosure.
Figure 4B:
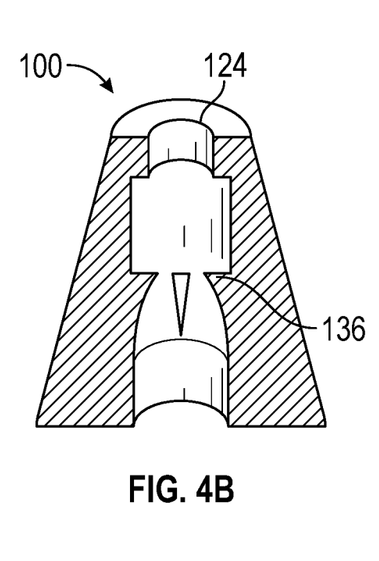
FIG. 4B is a cross-sectional view of the safety device of FIG. 4A taken along line B-B in accordance with an embodiment of the present disclosure.
Figure 4C:
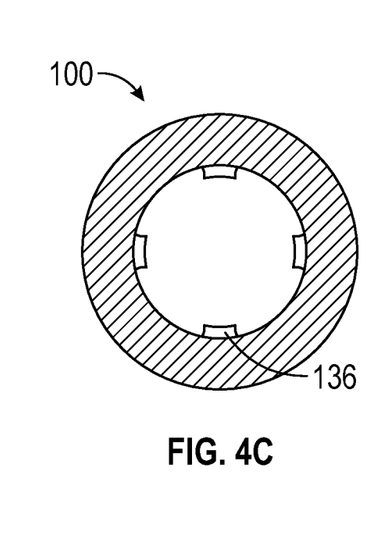
FIG. 4C is another cross-sectional view of the safety device of FIG. 4A taken along line C-C in accordance with an embodiment of the present disclosure.
Figure 5A:
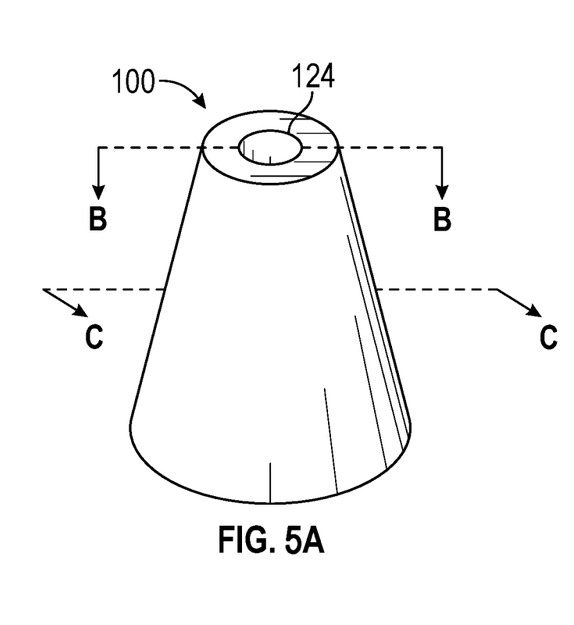
FIG. 5A is a perspective view of another safety device for removing and securing an intra-osseous device in accordance with an embodiment of the present disclosure.
Figure 5B:
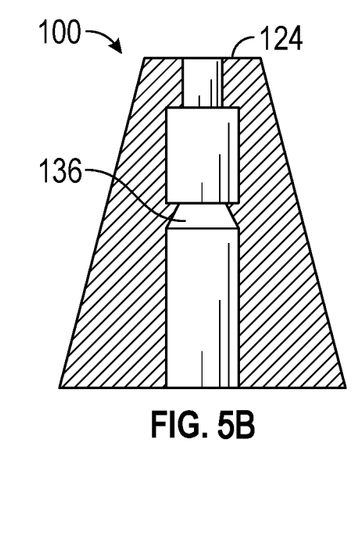
FIG. 5B is a cross-sectional view of the safety device of FIG. 5A taken along line B-B in accordance with an embodiment of the present disclosure.
Figure 5C:
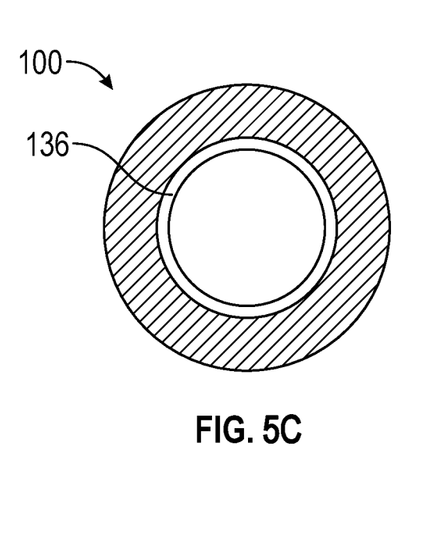
FIG. 5C is another cross-sectional view of the safety device of FIG. 5A taken along line C-C in accordance with an embodiment of the present disclosure.

With reference to FIGS. 4A-4C and FIGS. 5A-5C, the safety device 100 may have a frustum shape. The lock feature 136 can be in the form of a wedge with a ramp portion facing the first aperture 112 a shoulder portion facing the second aperture 124. In accordance with some embodiments of the present disclosure, for example as depicted in FIGS. 4B and 4C, the lock feature 136 can be provided as one or more discrete ramp members or wedges, spaced around the inner diameter of the containment chamber. Although four discrete ramp members are show in FIGS. 4B and 4C, any number of ramp members can be included. Moreover, the portion of the inner surface of the body 104 occupied by the ramp members can be varied. Where the lock feature 136 is provided as more than one discrete ramp member, the different ramp members can be positioned at the same distance from the first aperture. In accordance with other some embodiments of the present disclosure, for example as depicted in FIGS. 5B 5C, the lock feature 136 can extend around the inner diameter of the containment chamber to form a continuous ring. In accordance with still other embodiments of the present disclosure, the lock feature 136 can include a spring or other elastic member, alone or in combination with a moveable tab. In at least some embodiments, the lock feature 136 is formed as an integral part of the enclosure body 104. In accordance with at least some embodiments of the present disclosure, the enclosure body 104 is formed from single, integral piece of material. The material used to form the body 104 can be, for example, a nylon, plastic, polycarbonate, or other material.

The description of the present disclosure has been presented for purposes of illustration and description, but is not intended to be exhaustive or limiting of the disclosure to the form disclosed. Many modifications and variations will be apparent to those of ordinary skill in the art. The embodiments described and shown in the figures were chosen and described in order to best explain the principles of the disclosure, the practical application, and to enable those of ordinary skill in the art to understand the disclosure.

While various embodiments of the present disclosure have been described in detail, it is apparent that modifications and alterations of those embodiments will occur to those skilled in the art. Moreover, references made herein to "the invention" or aspects thereof should be understood to mean certain embodiments of the present disclosure and should not necessarily be construed as limiting all embodiments to a particular description. It is to be expressly understood that such modifications and alterations are within the scope and spirit of the present disclosure, as set forth in the following claims.

What is claimed is:

1. An apparatus for securing an intra-osseous device, comprising:
   a body extending from a first end to a second end;
   a cavity defined by an inner surface of the body, and the cavity extending between a first aperture at the first end of the body and a second aperture at the second end of the body;
   a lock feature positioned on the inner surface of the body, wherein the lock feature is positioned a first predetermined distance from the first end of the body; and
   a channel extending in the body from the first end to a distal point that is a second predetermined distance from the first end, wherein the second predetermined distance is larger than the first predetermined distance, wherein the lock feature extends continuously along the inner surface of the body between the channel and an additional channel.

2. The apparatus of claim 1, wherein the lock feature comprises a ramp portion oriented towards the first end of the body and comprises a shoulder portion oriented towards the second end of the body, wherein the shoulder portion extends from the inner surface of the body at a substantially perpendicular angle.

3. The apparatus of claim 2, wherein the ramp portion extends from the inner surface of the body at an angle between approximately 30 and 60 degrees.

4. The apparatus of claim 1, further comprising a relief aperture in the body positioned at the distal point of the channel, wherein the relief aperture has an outermost width that is larger than a width of the channel.

5. The apparatus of claim 1, wherein the channel extends in a direction that is substantially parallel to a longitudinal axis of the body.

6. The apparatus of claim 1, wherein a cross-sectional profile of the lock feature has a semi-circular shape.

7. A system for securing an intra-osseous device, comprising:
   a body extending from a first end to a second end;

a cavity defined by an inner surface of the body, and the cavity extending between a first aperture at the first end of the body and a second aperture at the second end of the body;

a lock feature positioned on the inner surface of the body, wherein the lock feature is positioned a predetermined distance from the first end of the body, and the lock feature defines an inner diameter;

an intra-osseous device having a base portion and a needle, wherein the base portion has an outermost diameter that is larger than the inner diameter defined by the lock feature, and wherein the intra-osseous device is configured to pass the lock feature such that the intra-osseous device is secured within the body and the needle is contained with the cavity; and wherein the second aperture has an inner diameter that is smaller than the outermost diameter of the base portion such that the intra-osseous device is retained within the body between the second aperture and the lock feature after the intra-osseous device passes the lock feature.

8. The system of claim 7, further comprising:
a syringe selectively connected to the intra-osseous device, the syringe having a barrel with an outer diameter that is smaller than the inner diameter of the second aperture.

9. The system of claim 8, wherein the inner diameter of the second aperture is between 1.1-1.2 times larger than the outer diameter of the barrel.

10. The system of claim 7, wherein an overall length of the intra-osseous device is smaller than an overall length of the body.

11. The system of claim 7, wherein a channel extends in the body from the first end to a distal point that is a second predetermined distance from the first end, wherein the second predetermined distance is larger than the predetermined distance of the lock feature.

12. A method for securing an intra-osseous device in a safety device, comprising:
providing an intra-osseous device with an outermost diameter;
providing a safety device having a body positioned about the intra-osseous device, wherein the body has an inner surface that defines a cavity extending between a first aperture at a first end of the body and a second aperture at a second end of the body, and wherein an inner diameter of the second aperture is smaller than the outermost diameter of the intra-osseous device;
providing a lock feature on the inner surface of the body, wherein the lock feature defines an inner diameter that is smaller than the outermost diameter of the intra-osseous device;
selectively connecting a syringe to the intra-osseous device, wherein the syringe has a barrel with an outer diameter that is less than the inner diameter of the second aperture;
drawing the intra-osseous device through the body of the safety device towards the second end;
deflecting the lock feature with the intra-osseous device such that the intra-osseous device passes the lock feature and is contained with the cavity, and
removing the syringe from the intra-osseous device after the intra-osseous device is secured between the lock feature and the second aperture.

13. The method of claim 12, wherein the intra-osseous device has an overall length, wherein the overall length of the intra-osseous device is smaller than an overall length of the body of the safety device.

14. The method of claim 12, further comprising:
providing a channel in the body of the safety device that extends from the first end to a distal point, wherein the channel allows the lock feature to deflect and permit the intra-osseous device to pass the lock feature.

15. The method of claim 14, wherein the lock feature is positioned a first predetermined distance from the first end of the body, and the distal point of the channel is a second predetermined distance from the first end of the body, wherein the second predetermined distance is larger than the first predetermined distance.

16. An apparatus for securing an intra-osseous device, comprising:
a body extending from a first end to a second end;
a cavity defined by an inner surface of the body, and the cavity extending between a first aperture at the first end of the body and a second aperture at the second end of the body;
a lock feature positioned on the inner surface of the body, wherein the lock feature is positioned a first predetermined distance from the first end of the body;
a channel extending in the body from the first end to a distal point that is a second predetermined distance from the first end, wherein the second predetermined distance is larger than the first predetermined distance; and
a relief aperture in the body positioned at the distal point of the channel, wherein the relief aperture has an outermost width that is larger than a width of the channel.

17. An apparatus for securing an intra-osseous device, comprising:
a body extending from a first end to a second end;
a cavity defined by an inner surface of the body, and the cavity extending between a first aperture at the first end of the body and a second aperture at the second end of the body;
a lock feature positioned on the inner surface of the body, wherein the lock feature is positioned a first predetermined distance from the first end of the body, wherein a cross-sectional profile of the lock feature has a semi-circular shape; and
a channel extending in the body from the first end to a distal point that is a second predetermined distance from the first end, wherein the second predetermined distance is larger than the first predetermined distance.

18. A system for securing an intra-osseous device, comprising:
a body extending from a first end to a second end;
a cavity defined by an inner surface of the body, and the cavity extending between a first aperture at the first end of the body and a second aperture at the second end of the body;
a lock feature positioned on the inner surface of the body, wherein the lock feature is positioned a predetermined distance from the first end of the body, and the lock feature defines an inner diameter, wherein a channel extends in the body from the first end to a distal point that is a second predetermined distance from the first end, wherein the second predetermined distance is larger than the predetermined distance of the lock feature; and
an intra-osseous device having a base portion and a needle, wherein the base portion has an outermost diameter that is larger than the inner diameter defined by the lock feature, and wherein the intra-osseous device is configured to pass the lock feature such that the intra-osseous device is secured within the body and the needle is contained with the cavity.

19. A method for securing an intra-osseous device in a safety device, comprising:
providing an intra-osseous device with an outermost diameter;
providing a safety device having a body positioned about the intra-osseous device, wherein the body has an inner surface that defines a cavity extending between a first aperture at a first end of the body and a second aperture at a second end of the body, and wherein an inner diameter of the second aperture is smaller than the outermost diameter of the intra-osseous device;
providing a channel in the body of the safety device that extends from the first end to a distal point;
providing a lock feature on the inner surface of the body, wherein the lock feature defines an inner diameter that is smaller than the outermost diameter of the intra-osseous device;
drawing the intra-osseous device through the body of the safety device towards the second end; and
deflecting the lock feature with the intra-osseous device such that the intra-osseous device passes the lock feature and is contained with the cavity, wherein the channel allows the lock feature to deflect and permit the intra-osseous device to pass the lock feature.

\* \* \* \* \*